(12) United States Patent
Szczepanik

(10) Patent No.: US 7,737,281 B2
(45) Date of Patent: *Jun. 15, 2010

(54) PURINE BASED FLUORESCENT DYES

(75) Inventor: Maciej Szczepanik, Huntington Station, NY (US)

(73) Assignee: Enzo Life Sciences, Inc. c/o Enzo Biochem, Inc., Farmingdale, NY (US)

( * ) Notice: Subject to any disclaimer, the term of this patent is extended or adjusted under 35 U.S.C. 154(b) by 1156 days.

This patent is subject to a terminal disclaimer.

(21) Appl. No.: 11/177,923

(22) Filed: Jul. 7, 2005

(65) Prior Publication Data

US 2006/0269931 A1    Nov. 30, 2006

Related U.S. Application Data

(63) Continuation-in-part of application No. 11/137,771, filed on May 24, 2005.

(51) Int. Cl.
*C07D 215/38* (2006.01)

(52) U.S. Cl. .................... 546/270.1; 546/16; 546/271.1

(58) Field of Classification Search .................. 546/16, 546/270.1, 271.1
See application file for complete search history.

(56) References Cited

U.S. PATENT DOCUMENTS

| | | | |
|---|---|---|---|
| 4,707,440 A | 11/1987 | Stavrianopoulos | |
| 4,868,103 A | 9/1989 | Stavrianopoulos et al. | |
| 4,937,198 A * | 6/1990 | Lee et al. ...................... | 436/94 |
| 5,047,519 A | 9/1991 | Hobbs, Jr. et al. | |
| 5,118,801 A | 6/1992 | Lizardi et al. | |
| 5,210,015 A | 5/1993 | Gelfand et al. | |
| 5,268,486 A * | 12/1993 | Waggoner et al. ........... | 548/427 |
| 5,401,847 A | 3/1995 | Glazer et al. | |
| 5,436,134 A | 7/1995 | Haugland et al. | |
| 5,486,616 A | 1/1996 | Waggoner et al. | |
| 5,538,848 A | 7/1996 | Livak et al. | |
| 5,569,766 A | 10/1996 | Waggoner et al. | |
| 5,580,990 A | 12/1996 | van den Berg et al. | |
| 5,646,264 A | 7/1997 | Glazer et al. | |
| 5,658,751 A | 8/1997 | Yue et al. | |
| 5,696,157 A | 12/1997 | Wang et al. | |
| 5,800,996 A | 9/1998 | Lee et al. | |
| 5,830,912 A | 11/1998 | Gee et al. | |
| 5,852,191 A | 12/1998 | Karandikar et al. | |
| 5,925,517 A | 7/1999 | Tyagi et al. | |
| 5,981,747 A | 11/1999 | Mujumdar et al. | |
| 5,994,056 A | 11/1999 | Higuchi | |
| 6,008,373 A | 12/1999 | Waggoner et al. | |
| 6,027,709 A | 2/2000 | Little et al. | |
| 6,110,630 A | 8/2000 | Reddy et al. | |
| 6,114,350 A | 9/2000 | Randall et al. | |
| 6,130,101 A | 10/2000 | Mao et al. | |
| 6,133,445 A | 10/2000 | Waggoner et al. | |
| 6,174,670 B1 | 1/2001 | Wittwer et al. | |
| 6,348,596 B1 | 2/2002 | Lee et al. | |
| 6,448,008 B1 * | 9/2002 | Caputo et al. ................... | 435/6 |
| 6,593,465 B1 | 7/2003 | Wolff et al. | |
| 6,664,047 B1 * | 12/2003 | Haugland et al. .............. | 435/6 |
| 6,686,145 B1 | 2/2004 | Waggoner et al. | |
| 6,953,148 B2 | 10/2005 | Esakov et al. | |
| 6,974,873 B2 | 12/2005 | Leung et al. | |
| 6,977,305 B2 | 12/2005 | Leung et al. | |
| 6,995,274 B2 | 2/2006 | Lugade et al. | |
| 7,446,202 B2 | 11/2008 | Dallwig et al. | |
| 2003/0225247 A1 | 12/2003 | Stavrianopoulos et al. | |
| 2006/0269926 A1* | 11/2006 | Xiang et al. .................... | 435/6 |
| 2006/0269931 A1 | 11/2006 | Szczepanik | |

FOREIGN PATENT DOCUMENTS

EP    0 231 495    8/1987

OTHER PUBLICATIONS

Moreda, Tetrahedron, vol. 53(37), pp. 12605-12614, 1997.*
Moreda, Tetrahedron, vol. 53(37), pp. 12595-12604, 1997.*
Ohnmacht, et al., Anal. Chem. 2006, 78:7547-7556, especially p. 7549.
Chapter 9.1 in Handbook of Molecular Probes and Research Chemicals, 6th Ed., 1996, Molecular Probes, Inc., Eugene OR.
Green, 1975, J. Histochem Cytochem., 23:411-423.
Kelly and Parker, 1981, J. Bact., 145:1017-1024.
Moreda and Forrester, Tetrahedron, 53:12595, 1997 and Tetrahedron, 53:12605, 1997.
U.S. Appl. No. 10/096,076.
U.S. Appl. No. 11/137,771, filed May 24, 2005.
U.S. Appl. No. 11/177,923, filed Jul. 7, 2005.

* cited by examiner

*Primary Examiner*—D. Margaret Seaman
(74) *Attorney, Agent, or Firm*—Ronald C. Fedus, Esq.; Natalie Bogdanos, Esq.

(57) ABSTRACT

The present invention provides novel purine-based fluorescent dyes that may be used for staining, localizing and otherwise labeling target molecules, such as nucleic acids, for detection, amplification and quantification.

23 Claims, 1 Drawing Sheet

PURINE BASED FLUORESCENT DYES

RELATED APPLICATIONS

This application is a continuation-in-part of U.S. patent application Ser. No. 11/137,771, filed on May 24, 2005. The entirety of the contents of Ser. No. 11/137,771 are hereby incorporated by reference.

FIELD OF THE INVENTION

This invention relates to a group of purine-based fluorescent dyes, and more particularly, relates to fluorescent dyes which preferentially stain nucleic acids.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

Fluorescent dyes that exhibit an enhanced fluorescence upon binding to DNA or RNA molecules are a basic tool in molecular and cell biology. Majority of the existing dyes bind noncovalently to nucleic acids through a combination of hydrophobic interactions with the DNA base-pairs and ionic binding to the negatively charged phosphate backbone. The most useful dyes are preferably non-fluorescent in the absence of the nucleic acids. Upon binding to DNA or RNA, however, several-fold fluorescence enhancement is measured, thereby enabling the detection of small amounts of nucleic acids.

A variety of fluorescent dyes have been shown to be effective stains for nucleic acids. Examples of fluorescent DNA-binding dyes include ethidium bromide, SYBR Green and SYBR Gold, which are commonly used to stain DNA in agarose gels, Hoechst 33258 and propidium iodide useful in flow cytometry or cell-impermeant TOTO dyes frequently used as a convenient indicator of apoptosis. Selected properties of these dyes such as the brightness, spectral properties, resistance to photobleaching, affinity for either single or double stranded nucleic acids can be modified to some extend with changing the type and location of the substituents.

In order for a fluorescent dye to be a useful tool in molecular and cell biology, the dye has to meet several requirements. First, it should preferably have an excitation maximum between 300 and 900 nm, with a Stoke shift of at least 10 nm. The most preferable dyes have an excitation maximum between 500 and 900 nm. This spectroscopic range is both compatible with the existing detection instrumentation and removed from any other interfering biological molecules. Fluorescent dyes used in nucleic acid research should also have a high molar extinction coefficient, a high quantum yield, good photostability, and significantly increased fluorescence when bound to nucleic acids.

In U.S. Pat. No. 4,937,198, a purine-based fluorescent dye was disclosed that selectively stained nucleic acids. The dye was reported to have a molar extinction coefficient of 60,000 $M^{-1}$ $cm^{-1}$, quantum yield of 0.4 and excitation maximum in the presence of nucleic acids around 460 nm with an emission maximum around 478 nm. Fluorescence enhancement of over 7,000-fold was measured upon binding of the dye to RNA.

Moreda and Forrester (Tetrahedron, 53, 12595, 1997 and Tetrahedron, 53, 12605, 1997) described a synthesis and characterization of a range of purine-based fluorescent dyes that were used as fluorescent dyes for DNA marking in the diagnosis of malaria parasites.

SUMMARY OF THE INVENTION

The present application discloses novel purine-based dyes and their methods of preparation. In a preferred embodiment, the dyes are capable of selectively staining DNA and RNA, thereby providing high sensitivity for detection of nucleic acids in solution or by gel analysis. Upon binding of the dyes of the present invention to nucleic acids, fluorescence enhancement in excess of 1000-fold has been observed. Exemplary dyes showed a maximum absorbance upon binding to nucleic acids around 460-470 nm, and a broad fluorescence emission between 470 and 530 nm. Some of the described dyes are characterized by the presence of a polycationic chain that may contribute towards a high binding affinity towards nucleic acids, and others contain lipophylic moieties rendering the dyes membrane permeable.

DESCRIPTION OF THE INVENTION

Figure 1:
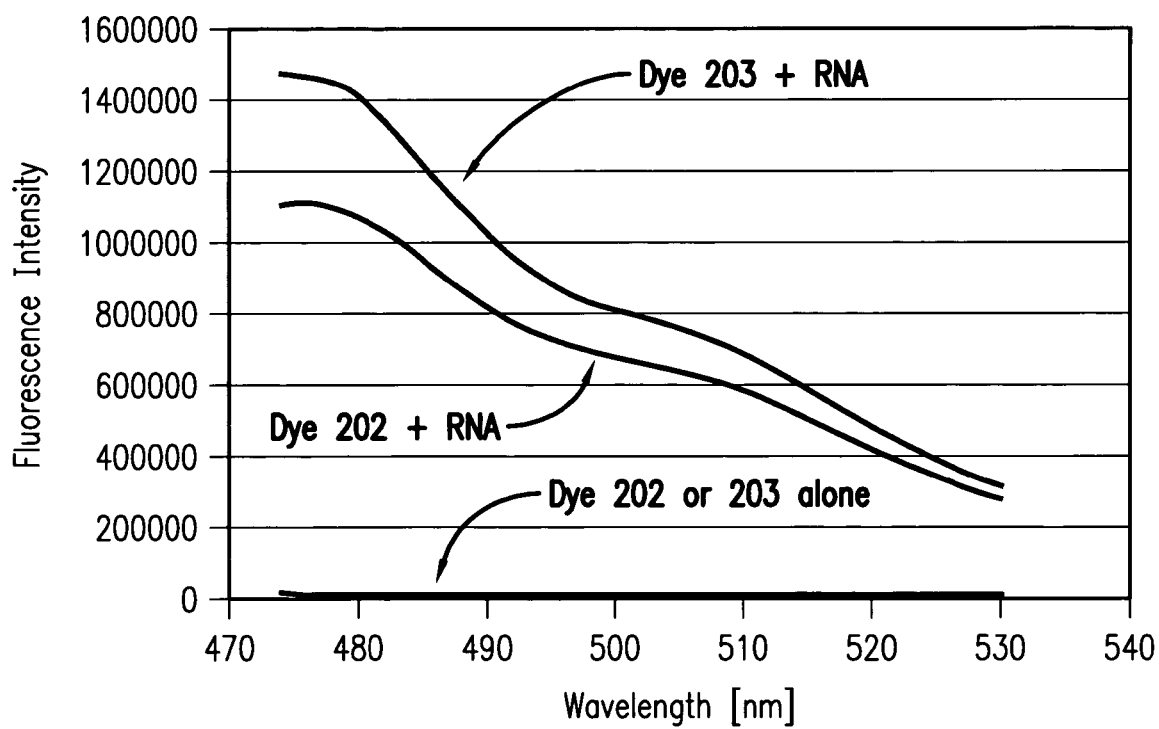
FIG. 1 illustrates a fluorescence enhancement of Dye 202 and Dye 203 upon binding RNA. The experiment was carried out with concentration of RNA 100 M/ml and 0.5 M Dye 202 or 203.

The present invention describes a group of novel, purine-based fluorescent dyes that may be used as labels. In a preferred embodiment, the novel dyes are excitable around 460-470 nm, emit maximally around 470-480 nm and selectively stain nucleic acids. In the absence of nucleic acids, these particular dyes are essentially non-fluorescent. However, upon binding to nucleic acids, fluorescence enhancement in excess of 1000-fold has been observed. The dyes are selective towards nucleic acids, as only a very modest fluorescence enhancement is generated by the presence of proteins.

The dyes of the invention comprise three portions: a first portion comprising a purinium ring system, a second portion comprising an aromatic ring system and a third portion which comprises a methine bridge joining the first and second portions. Examples of heterocyclic ring systems that may be used for the second portion can include but not be limited to benzazolium, pyridinium, quinolinium, lepidinium, acrydinium, pyrylium and thiopyrylium rings.

In one embodiment of the present invention, a purinium ring system is joined to a benzazolium moiety and further comprises a charged or polar group as described in U.S. patent application Ser. No. 11/137,771 (filed May 24, 2005). As such these dyes have the structure:

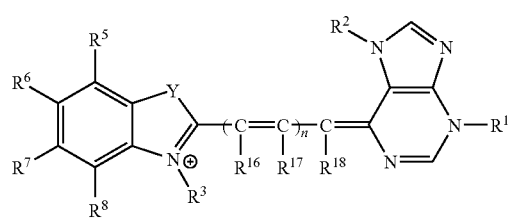

wherein n can be 0, 1 or 2;

wherein Y comprises $CR^{10}R^{11}$, $NR^{10}$, O, S or Se where $R^{10}$ and $R^{11}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{10}$ and $R^{11}$ form a 5 or 6 membered ring;

wherein at least one of $R^1$, $R^2$, $R^3$, $R^5$, $R^6$, $R^7$, $R^8$, $R^{16}$, $R^{17}$ or $R^{18}$ comprises Q; wherein Q comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$), a phosphonate monoester ($PO_2^-ER^{13}$), a phosphonate diester ($POER^{13}ER^{14}$), a thiophosphate ($PSO_3^-$), a thiophosphate monoester ($PSO_2^-ER^{13}$), a thiophosphate diester ($PSOER^{13}ER^{14}$), a thiophosphonate ($PSO_2^=$), a thiophosphonate monoester ($PSO^-ER^{13}$), a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S;

wherein Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

wherein the remaining $R^1$, $R^2$, $R^3$, $R^5$, $R^6$, $R^7$, $R^8$, $R^{16}$, $R^{17}$ and $R^{18}$ independently comprise hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^{16}$ and $R^3$, $R^3$ and $R^8$, $R^8$ and $R^7$, $R^7$ and $R^6$, $R^6$ and $R^5$, $R^5$ and $R^{10}$, $R^{16}$ and $R^{17}$, $R^{10}$ and $R^{16}$, and $R^{17}$ and $R^{18}$ may form a 5 or 6 membered ring;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$), a phosphonate monoester ($PO_2^-ER^{13}$), a phosphonate diester ($POER^{13}ER^{14}$), a thiophosphate ($PSO_3^-$), a thiophosphate monoester ($PSO_2^-ER^{13}$), a thiophosphate diester ($PSOER^{13}ER^{14}$), a thiophosphonate ($PSO_2^=$), a thiophosphonate monoester ($PSO^-ER^{13}$), a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R^1$, $R^2$, $R^3$, $R^5$, $R^6$, $R^7$, $R^8$, $R^{16}$, $R^{17}$ and $R^{18}$ may independently further comprise a heteroatom containing side chain wherein said side chain is joined to the R group by a linkage which comprises an ether linkage ($-OR^{25}$), a thioether linkage ($-SR^{25}$), or an amine linkage ($-NR^{25}R^{26}$ or $-N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain.

In prior art, benzazolium moieties have been joined to purinium rings (U.S. Pat. No. 4,937,198, and Moreda and Forrester supra) but without the advantages endowed by the presence of the charged or polar groups described as Q above.

In another embodiment of the present invention, the second portion joined to the purinium first portion results in dyes with the structure:

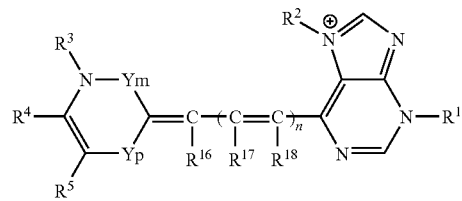

wherein n is 0, 1 or 2;
wherein Y is $-CR^6=CR^7-$;
wherein m and p have values of 0 or 1 and m+p=1;
wherein $R^1$, $R^2$, $R^3$, $R^4$, $R^5$, $R^6$, $R^7$, $R^{16}$, $R^{17}$ and $R^{18}$ independently comprise hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, a combination or combinations of $R^1$, $R^2$, $R^3$, $R^4$, $R^5$, $R^6$, $R^7$, $R^{16}$, $R^{17}$ and $R^{18}$ form one or more 5 or 6 membered rings;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$), a phosphonate monoester ($PO_2^-ER^{13}$), a phosphonate diester ($POER^{13}ER^{14}$), a thiophosphate ($PSO_3^-$), a thiophosphate monoester ($PSO_2^-ER^{13}$), a thiophosphate diester ($PSOER^{13}ER^{14}$), a thiophosphonate ($PSO_2^=$), a thiophosphonate monoester ($PSO^-ER^{13}$), a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R^1$, $R^2$, $R^3$, $R^4$, $R^5$, $R^6$, $R^7$, $R^{16}$, $R^{17}$ and $R^{18}$ may independently further comprise a heteroatom containing side chain wherein said side chain is joined to the R group by a linkage which comprises an ether linkage ($-OR^{25}$), a thioether linkage ($-SR^{25}$), or an amine linkage ($-NR^{25}R^{26}$ or $-N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain.

In this aspect of the present invention, the dyes described above may enjoy the benefits of being modified by groups described as Z or they may be used without such groups.

In another embodiment of the present invention, a different aromatic group is chosen as the second portion resulting in a composition with the structure:

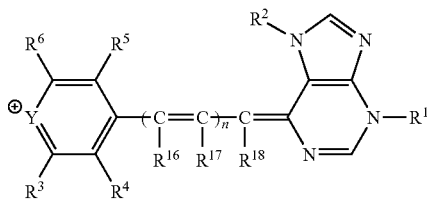

wherein n is 0, 1 or 2;

wherein Y is either S or O;

wherein $R^1$, $R^2$, $R^3$, $R^4$, $R^5$, $R^6$, $R^{16}$, $R^{17}$ and $R^{18}$ independently comprise hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, a combination or combinations of $R^1$, $R^2$, $R^3$, $R^4$, $R^5$, $R^6$, $R^{16}$, $R^{17}$ and $R^{18}$ form one or more 5 or 6 membered rings;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$), a phosphonate monoester ($PO_2^-ER^{13}$), a phosphonate diester ($POER^{13}ER^{14}$), a thiophosphate ($PSO_3^=$), a thiophosphate monoester ($PSO_2^-ER^{13}$), a thiophosphate diester ($PSOER^{13}ER^{14}$), a thiophosphonate ($PSO_2^=$), a thiophosphonate monoester ($PSO^-ER^{13}$), a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R^1$, $R^2$, $R^3$, $R^4$, $R^5$, $R^6$, $R^{16}$, $R^{17}$ and $R^{18}$ may independently further comprise a heteroatom containing side chain wherein said side chain is joined to the R group by a linkage which comprises an ether linkage ($—OR^{25}$), a thioether linkage ($—SR^{25}$), or an amine linkage ($—NR^{25}R^{26}$ or $—N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain.

In this aspect of the present invention, the dyes described above may enjoy the benefits of being modified by groups described as Z or they may be used without such groups.

In another embodiment of the present invention, a benzazole group is chosen as the second portion and the methine group is modified by bridging a portion of it to the benzazole moiety resulting in a composition with the structure:

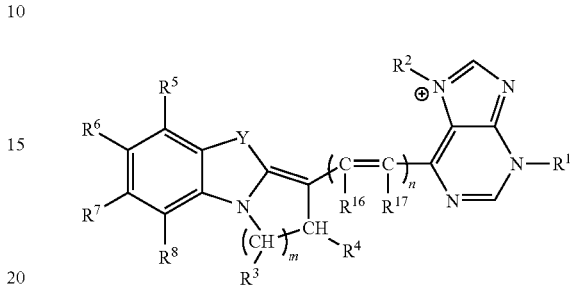

wherein m is 1, 2, 3, or 4;

wherein n is 0, 1 or 2;

wherein Y comprises $CR^{10}OR^{11}$, $NR^{10}$, O, S or Se where $R^{10}$ and $R^{11}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{10}$ and $R^{11}$ form a 5 or 6 membered ring;

wherein $R^1$, $R^2$, $R^3$, $R^4$, $R^5$, $R^6$, $R^7$, $R^8$, $R^{16}$ and $R^{17}$ independently comprise hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, a combination or combinations of $R^1$, $R^2$, $R^3$, $R^4$, $R^5$, $R^6$, $R^7$, $R^8$, $R^{16}$, and $R^{17}$ form one or more 5 or 6 membered rings;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$), a phosphonate monoester ($PO_2^-ER^{13}$), a phosphonate diester ($POER^{13}ER^{14}$), a thiophosphate ($PSO_3^=$), a thiophosphate monoester ($PSO_2^-ER^{13}$), a thiophosphate diester ($PSOER^{13}ER^{14}$), a thiophosphonate ($PSO_2^=$), a thiophosphonate monoester ($PSO^-ER^{13}$), a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R^1$, $R^2$, $R^3$, $R^4$, $R^5$, $R^6$, $R^7$, $R^8$, $R^{16}$, and $R^{17}$ may independently further comprise a heteroatom containing side chain wherein said side chain is joined to the R group by a linkage which comprises an ether linkage ($—OR^{25}$), a thioether linkage ($—SR^{25}$), or an amine linkage ($-NR^{25}R^{26}$ or $-N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain.

In this aspect of the present invention, the dyes described above may enjoy the benefits of being modified by groups described as Z or they may be used without such groups. Rigidization of the methine bond has been previously described in joining together two benzazolium moieties (U.S. Pat. Nos. 6,133,445 and 6,686,145 both of which are hereby incorporated by reference) but has not been previously described in joining a benzazolium to a purinium dye.

The novel dyes of the present invention may be used for any purposes previously described for fluorescent dyes. For example, these dyes may be modified with a reactive group to attach them to target molecules of interest. These dyes may also be used free in solution and advantage taken of their ability to bind to target molecules of interest. Of especial use is when this binding event results in an increase in fluorescence of the dye molecules. For further examples of use, reference is made to U.S. patent application Ser. No. 11/137,771 filed May 24, 2005, hereby incorporated by reference.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

EXAMPLE 1

Synthesis of Dye 201

(a) Preparation of 4-(Sulfobutyl)-2-methylbenzothiazole (Compound 1)

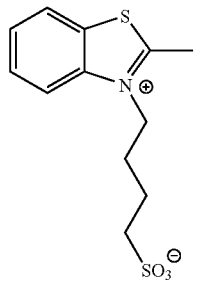

A mixture of 2-methylbenzothiazole (1.49 g, 10 mmol) and 1,4-butane sultone (4.0 g, 30 mmol) was heated in a pressure tube at 130-140° C. for 3 hours. The mixture was allowed to cool to room temperature, and the resulting mass was triturated with ethyl acetate (50 ml) until a gray solid separated. The solid was collected by centrifugation, washed with ethyl acetate and dried under vacuum to yield 2.8 g (96%) of Compound 1.

(b) Preparation of 3-Methyl-6-(methylthio)purine (Compound 2)

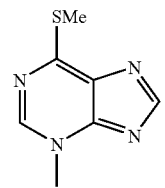

Compound 2 was prepared as described in U.S. Pat. No. 4,937,198 (herein incorporated by reference). The structure of this compound is given above.

(c) Preparation of 7-(Iodopropyl)-3-methyl-6-(methylthio)purinium iodide (Compound 3)

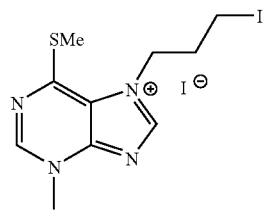

A pressure tube, equipped with a magnetic stirring bar, was charged with Compound 2 (0.54 g, 3 mmole) and 1,3-diiodopropane (2.66 g, 9 mmole). The mixture was heated to ~120° C. for 3 hours. The residue was extensively washed with ethyl acetate and diethyl ether and dried under vacuum to give 0.4 g of yellow solid Compound 3 (yield ~28%).

(d) Preparation of Dye 201

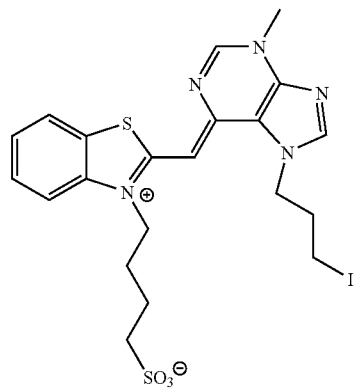

To a pear-shaped flask, equipped with a magnetic stirring bar and a reflux condenser, were added Compound 1 (72 mg, 250 mole), Compound 3 (120 mg, 250 mole), 2 ml of methanol and 42 l of triethylamine. The mixture was refluxed for about 45 minutes, producing a red solution containing an orange solid. The contents of the flask were cooled and the reaction mixture was added to 50 ml ethyl acetate. The resulting yellow precipitate was centrifuged and extensively washed with ethyl acetate. The residue was dried under vacuum to give the title compound (55% yield).

EXAMPLE 2

Synthesis of Dye 202

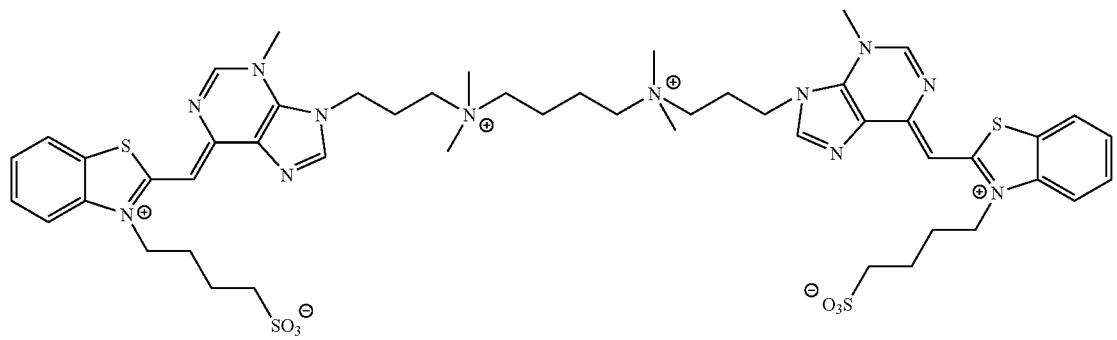

A mixture of Dye 201 obtained in Example 1 (50 mg, 70 mole), N,N,N',N'-tetramethyldiaminobutane (6.5 l, 35 mole) and 3 ml of ethanol was refluxed for 2 hours, producing a red solution. The contents of the flask were cooled and the reaction mixture was added to 50 ml ethyl acetate. The resulting red precipitate was centrifuged and extensively washed with ethyl acetate followed by washing with diethyl ether. The residue was dried under vacuum to give Dye 202 (48% yield).

EXAMPLE 3

Synthesis of Dye 203

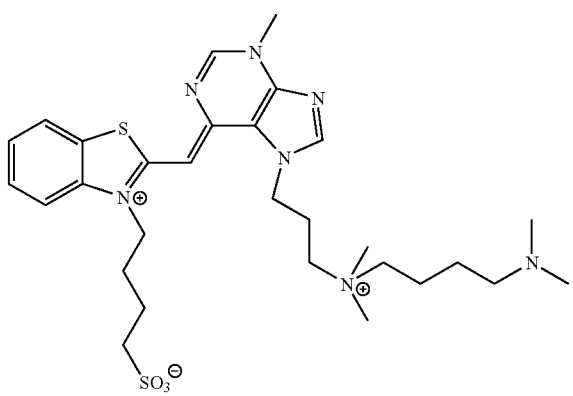

A pear-shaped flask, equipped with a magnetic stirring bar and a reflux condenser, was charged with—Compound 1 from step (a) of Example 1 (90 mg, 315 mole), Compound 3 from step (c) of Example 1 (150 mg, 315 mole), N,N,N',N'-tetramethyldiaminobutane (0.58 ml, 3.15 mmole) and 2.5 ml of methanol. The mixture was refluxed for about 2 hours, producing a brownish solution containing an orange solid. The contents of the flask were cooled and the reaction mixture was added to 50 ml ethyl acetate. The resulting brown precipitate was centrifuged and extensively washed with ethyl acetate. The residue was dried under vacuum to give Dye 203 (67% yield).

EXAMPLE 4

Synthesis of Dye 204

(a) Preparation of N-(2,3-dimethylbenzothiazole-6-sulfonyl)piperidine tosylate (compound 4)

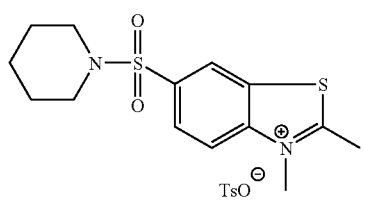

Compound 4 was prepared as described in U.S. patent application Ser. No. 11/137,771 filed May 24, 2005 (herein incorporated by reference). The structure of this compound is given above.

(b) Preparation of 3,7-Dimethyl-6-(methylthio)purinium tosylate (Compound 5)

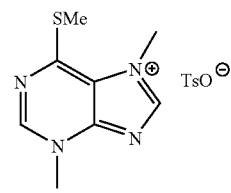

Compound 5 was prepared as described in U.S. Pat. No. 4,937,198 (herein incorporated by reference). The structure of this compound is given above.

(c) Preparation of Dye 204

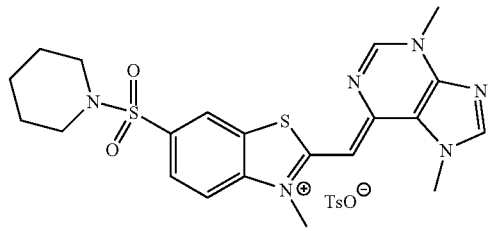

A mixture of Compound 4 (64 mg, 136 mole), Compound 5 (50 mg, 136 mole) and 20 l of triethylamine was refluxed for about 1 hour, producing an orange solution. The contents of the flask were cooled and the reaction mixture was added to 50 ml ethyl acetate. The resulting orange precipitate was centrifuged and extensively washed with ethyl acetate. The residue was dried under vacuum to give Dye 204 (61% yield).

EXAMPLE 5

Interaction of Dyes 202 and 203 with Nucleic Acids a) Absorbance Measurements

Dyes 202 and 203 were dissolved in DMSO to give 609 M and 1.35 mM solutions, respectively. These stock solutions were diluted to a dye concentration of 20 M either with water alone or with water containing RNA (S. cerevisiae, Sigma-Aldrich) at a concentration of 1 mg/ml and absorbance readings were taken. The absorbance maximum in the absence of RNA was at 452 nm, while the maximum in the presence of RNA was shifted to 462 nm.

b) Emission Measurements

The above mentioned stocks were diluted with DMSO to prepare 100 M solutions of Dyes 202 and 203. Subsequently, 5 l of dye solution was mixed with either 995 l of RNase-free water or 995 l water containing 100 l RNA (1 mg/ml). The solutions were incubated for 5 minutes at room temperature and the fluorescence emission was measured with an excitation wavelength of 463 nm. As seen in FIG. 1, virtually no fluorescence was observed in the absence of RNA while a broad emission curve was measured for RNA-dye complexes.

EXAMPLE 6

Interaction of Dyes 202 and 203 with Proteins

Dyes 202 and 203 stock solutions from Example 5 were diluted with water to give 100 M solutions of Dyes 202 and 203. Subsequently, 5 l of the 100 M dye solution was incubated in 10 mM TrisXHCl buffer (pH 7.2) in the absence or in the presence of 1 ml of 100 g/ml of BSA, lysozyme or casein. The fluorescence emission was measured with an excitation wavelength of 463 nm. Virtually no fluorescence was observed in the absence of proteins. When the dyes were incubated in the presence of proteins only a modest increase in fluorescence intensity was recorded (data not shown) indicating essentially a lack of signal by the presence of proteins and a specificity of signal enhancement by nucleic acids for these dyes.

FIG. 1

Many obvious variations will be suggested to those of ordinary skill in the art in light of the above detailed descriptions of the present invention. All such obvious variations are fully contemplated and are embraced by the scope and spirit of the present invention as set forth in the claims that now follow.

What is claimed is:

1. A dye having the formula:

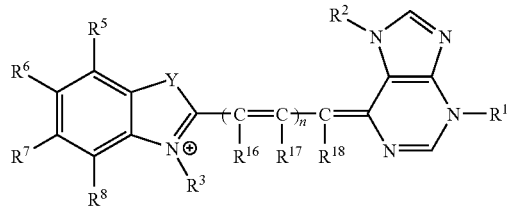

wherein n is 0, 1 or 2;

wherein Y comprises $CR^{10}R^{11}$, $NR^{10}$, O, S or Se where $R^{10}$ and $R^{11}$ independently comprise hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^{10}$ and $R^{11}$ form a 5 or 6 membered ring;

wherein at least one of $R^1$, $R^2$, $R^3$, $R^5$, $R^6$, $R^7$, $R^8$, $R^{16}$, $R^{17}$ or $R^{18}$ comprises Q;

wherein Q comprises a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$), a phosphonate monoester ($PO_2^-ER^-$), a phosphonate diester ($POER^{13}ER^{14}$), a thiophosphate ($PSO_3^=$), a thiophosphate monoester ($PSO_2^-ER^{13}$), a thiophosphate diester ($PSOER^{13}ER^{14}$), a thiophosphonate ($PSO_2^=$), a thiophosphonate monoester ($PSO^-ER^{13}$), a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a thioanalogue of phosphoramidite ($POSR^{19}NR^{13}R^{14}$), wherein any of E can independently comprise O or S;

wherein Q is attached directly, or indirectly through a linker arm comprising carbon, sulfur, oxygen, nitrogen, or any combinations thereof, and wherein said linker arm may be saturated or unsaturated, linear or branched, substituted or unsubstituted, or any combinations thereof;

wherein the remaining $R^1$, $R^2$, $R^3$, $R^5$, $R^6$, $R^7$, $R^8$, $R^{16}$, $R^{17}$ and $R^{18}$ independently comprise hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^{16}$ and $R^3$, $R^3$ and $R^8$, $R^8$ and $R^7$, $R^7$ and $R^6$, $R^6$ and $R^5$, $R^5$ and $R^{10}$, $R^{16}$ and $R^{17}$, $R^{10}$ and $R^{16}$, and $R^{17}$ and $R^{18}$ may form a 5 or 6 membered ring;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$), a phosphonate monoester ($PO_2^-ER^{13}$), a phosphonate diester ($PO_2ER^{13}ER^{14}$), a thiophosphate ($PSO_3^=$), a thiophosphate monoester ($PSO_2^-ER^{13}$), a thiophosphate diester ($PSOER^{13}ER^{14}$), a thiophosphonate ($PSO_2^=$), a thiophosphonate monoester ($PSO^-ER^{13}$), a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$), wherein any of E can independently comprise O or S;

wherein Z is attached directly, or indirectly through a linker arm comprising carbon, sulfur, oxygen, nitrogen, or any combinations thereof, and wherein said linker arm may be saturated or unsaturated, linear or branched, substituted or unsubstituted, or any combinations thereof;

and wherein any of $R^1$, $R^2$, $R^3$, $R^5$, $R^6$, $R^7$, $R^8$, $R^{16}$, $R^{17}$ and $R^{18}$ may independently further comprise a heteroatom containing side chain wherein said side chain is joined to said R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain.

2. The dye of claim 1, wherein at least one of $R^1$, $R^2$, $R^3$, $R^5$, $R^6$, $R^7$, $R^8$, $R^{10}$, $R^{11}$, $R^{13}$, $R^{14}$, $R^{15}$, $R^{16}$, $R^{17}$ or $R^{18}$ comprises a reactive group.

3. The dye of claim 2, wherein said reactive group comprises a nucleophilic reactive group, an electrophilic reactive group, a terminal alkene, a terminal alkyne, a coordinate group or an alkylating agent.

4. The dye of claim 3, wherein said nucleophilic reactive group comprises a thiol, amine, hydrazine or hydroxyl group.

5. The dye of claim 3, wherein said electrophilic reactive group comprises an isocyanate, isothiocyanate, monochlorotriazine, dichlorotriazine, 4,6-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, azidonitrophenol, azide, 3-(2-pyridyl dithio)proprionamide, glyoxal or aldehyde group.

6. The dye of claim 1, wherein said dye is linked to a target molecule.

7. The dye of claim 6, wherein said target molecule comprises a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, strepavidin, digoxygenin, carbohydrate, oligosaccharide, polysaccharide, lipid, glycolipid, viral particle, viral component, bacterial cell, bacterial component, eucaryotic cell, eukaryotic cell component, natural drug, synthetic drug, glass particle, glass surface, plastic particle, plastic surface, siliceous particle, siliceous surface, organic molecule, dye or a derivative thereof.

8. The dye of claim 7, wherein said nucleoside, nucleotide, oligonucleotide, or polynucleotide comprises one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues or any combination thereof.

9. The dye of claim 6, wherein said dye is linked to said target molecule through a linker arm.

10. The dye of claim 9, wherein said linker arm is attached to said target molecule through a bond which comprises a covalent bond, a non-covalent bond, a polar bond or a coordinate bond.

11. The oligonucleotide or polynucleotide of claim 8, wherein said oligonucleotide or polynucleotide comprises two or more dye molecules attached to separate nucleotides of said oligonucleotide or polynucleotide.

12. The oligonucleotide or polynucleotide of claim 11, wherein said two or more dye molecules comprise the same dye molecules.

13. The oligonucleotide or polynucleotide of claim 11, wherein said two or more dye molecules comprise different dye molecules.

14. A composite dye comprising the dye of claim 7, said dye being joined or attached to a second dye molecule.

15. The dye of claim 1, wherein said dye is attached to a target specific moiety.

16. The dye of claim 15, wherein said target specific moiety comprises a protein or a nucleic acid.

17. The dye of claim 16, wherein said protein comprises an antibody or a fragment thereof.

18. The dye of claim 16, wherein said nucleic acid comprises unmodified nucleotides, modified nucleotides, nucleotide analogues or any combination thereof.

19. The dye of claim 1, wherein said alkyl or alkoxy groups independently comprise from 1-18 carbons.

20. The dye of claim 19, wherein said alkyl or alkoxy groups independently comprise from 1-6 carbons.

21. The dye of claim 3 wherein said electrophilic reactive group comprises an isocyanate, isothiocyanate, monochlorotriazine, dichlorotriazine, 4,6-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, azidonitrophenol, azide, 3-(2-pyridyl dithio)proprionamide, glyoxal or aldehyde group.

22. A dye having the formula
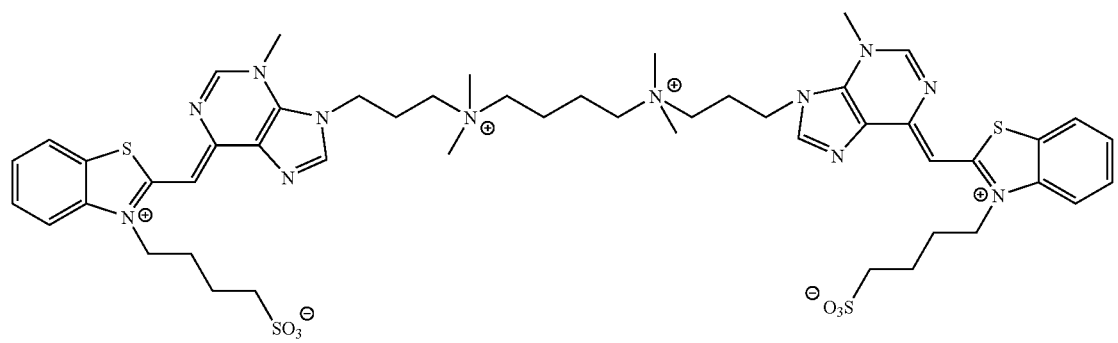
or
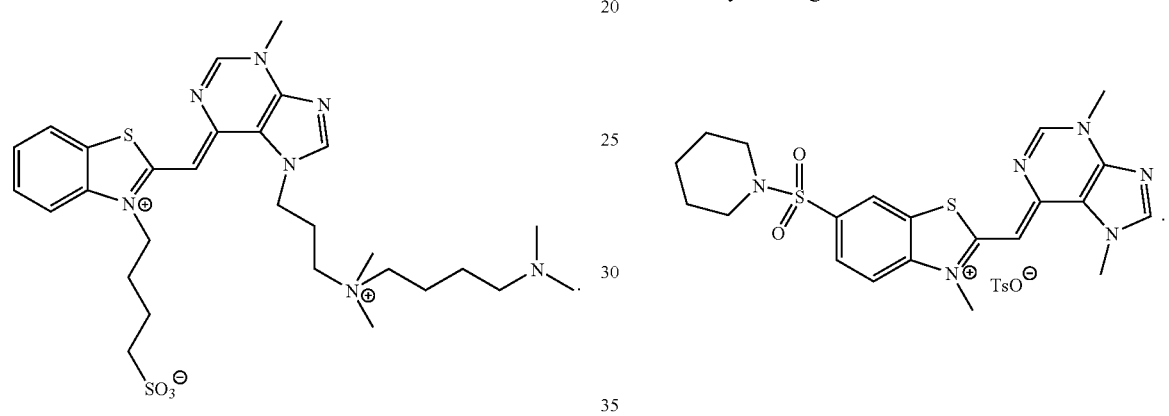
23. A dye having the formula
* * * * *